(12) United States Patent
Moon et al.

(10) Patent No.: US 12,390,107 B2
(45) Date of Patent: Aug. 19, 2025

(54) SYSTEMS AND APPARATUSES FOR THREE-DIMENSIONAL EYE IMAGING FOR SCREENING, MONITORING, AND DIAGNOSIS OF DISEASES

(71) Applicant: EYENUK, INC., Woodland Hills, CA (US)

(72) Inventors: Ji Sun Moon, Oakland, CA (US); Gregory John Alexander Russell, Woodland Hills, CA (US); Kaushal Mohanlal Solanki, West Hills, CA (US); Malavika Bhaskaranand, West Hills, CA (US); Chaithanya Ramachandra, West Hills, CA (US)

(73) Assignee: EYENUK, INC., Woodland Hills, CA (US)

( * ) Notice: Subject to any disclaimer, the term of this patent is extended or adjusted under 35 U.S.C. 154(b) by 712 days.

(21) Appl. No.: 17/478,673

(22) Filed: Sep. 17, 2021

(65) Prior Publication Data

US 2022/0079436 A1 Mar. 17, 2022

Related U.S. Application Data

(60) Provisional application No. 63/079,966, filed on Sep. 17, 2020.

(51) Int. Cl.
*A61B 3/14* (2006.01)
*A61B 3/12* (2006.01)
*A61B 3/15* (2006.01)

(52) U.S. Cl.
CPC ............. *A61B 3/158* (2013.01); *A61B 3/12* (2013.01); *A61B 3/14* (2013.01)

(58) Field of Classification Search
CPC .............. A61B 3/12; A61B 3/14; A61B 3/158
USPC .......................... 351/206, 211, 214
See application file for complete search history.

(56) References Cited

U.S. PATENT DOCUMENTS

| 8,109,635 | B2 * | 2/2012 | Allon ................. A61B 3/12 351/221 |
| 11,875,480 | B1 * | 1/2024 | Kavusi ................ G06T 7/11 |
| 2013/0128223 | A1 * | 5/2013 | Wood ................. A61B 3/1208 351/246 |
| 2015/0374233 | A1 * | 12/2015 | Zhang ................ A61B 3/14 351/246 |
| 2020/0015676 | A1 * | 1/2020 | Glik .................. A61B 3/156 |

FOREIGN PATENT DOCUMENTS

WO WO 2020/112757 6/2020

\* cited by examiner

*Primary Examiner* — Mahidere S Sahle
(74) *Attorney, Agent, or Firm* — ONE LLP

(57) ABSTRACT

Disclosed are example embodiments of a system of retinal three-dimensional (3D) imaging. The system of retinal 3D imaging includes an image sensor within a light path and a reimaging corrective optics module within the light path. The system of retinal 3D imaging also includes an objective lens in the light path and a baffle-and-illumination module in the light path. In an aspect, the reimaging corrective optics module is in front of the image sensor, the objective lens is in front of the reimaging corrective optics module, and the baffle-and-illumination module is between the objective lens and the reimaging corrective optics module.

15 Claims, 6 Drawing Sheets

SYSTEMS AND APPARATUSES FOR THREE-DIMENSIONAL EYE IMAGING FOR SCREENING, MONITORING, AND DIAGNOSIS OF DISEASES

CLAIM OF PRIORITY UNDER 35 U.S.C. & 120

The present application for patent claims priority to U.S. Provisional Patent Application No. 63/079,966, filed Sep. 17, 2020, and assigned to the assignee hereof and hereby expressly incorporated by reference herein.

FIELD

The present disclosure relates generally to the field of retinal Three-dimension ("3D") imaging and more specifically to systems and methods for retinal 3D imaging to screen, diagnose, and monitor eye diseases or disorders such as glaucoma, age-related macular degeneration, diabetic retinopathy, diabetic macular edema, papilledema, retinopathy of prematurity.

BACKGROUND

Currently, the estimated number of glaucoma patients worldwide is 64 million and this number is expected to grow to 112 million by 2040. However, the number of ophthalmologists in the world is orders of magnitude smaller than the number needed to screen, manage, and treat this number of patients. 3D topographic information of a retina (e.g., optic disc) of an eye may provide information for early diagnosis of glaucoma. In addition to glaucoma, 3D imaging can provide information for screening or diagnosis of other conditions such as age-related macular degeneration, diabetic retinopathy, retinopathy of prematurity, papilledema, diabetic macular edema, risk for cardiovascular diseases, risk for stroke, and neurodegenerative disorders such as Alzheimer's disease. Multiple types of 3D images acquired from various imaging equipment such as optical coherent tomography, scanning laser topography and fundus camera stereo images may provide 3D topographic information of a retina. However, accessibility to such imaging systems is often limited by either their high equipment cost or difficult usability.

SUMMARY OF THE INVENTION

Provided herein are example embodiments of systems, devices, and methods for retinal 3D imaging to screen, diagnose, and monitor eye diseases such as glaucoma. Structured light 3D imaging technology has been successfully adapted and used for various applications including metrologies and consumer electronics (e.g., smartphones) by providing high image resolutions, wide depth ranges, high speed image captures, high speed image processing, and small device form factors. The systems disclosed herein use 3D structured light imaging technology to lower the manufacturing cost of the equipment for 3D retinal imaging while providing sufficient image quality and easy operation to enable a greater accessibility of screening, diagnosis, and monitoring of eye diseases. The images acquired by systems for 3D retinal imaging may be processed to reconstruct the 3D topographic images first and the reconstructed 3D topographic images may subsequently be analyzed by artificial intelligence (AI) algorithms or human eye specialists to screen, diagnose and monitor eye diseases. The acquired images by systems for 3D retinal imaging may be analyzed directly without processing into 3D topographic images.

One general aspect includes a system of retinal three-dimensional (3D) imaging. The system of retinal 3D imaging includes an image sensor within a light path. The system of retinal 3D imaging also includes a reimaging corrective optics module within the light path. The system of retinal 3D imaging also includes an objective lens in the light path. The system of retinal 3D imaging also includes a baffle-and-illumination module in the light path.

BRIEF DESCRIPTION OF THE DRAWINGS

The details of the subject matter set forth herein, both as to its structure and operation, may be apparent by study of the accompanying figures, in which like reference numerals refer to like parts. The components in the figures are not necessarily to scale, emphasis instead being placed upon illustrating the principles of the subject matter. Moreover, all illustrations are intended to convey concepts, where relative sizes, shapes and other detailed attributes may be illustrated schematically rather than literally or precisely.

DETAILED DESCRIPTION

Figure 1A:
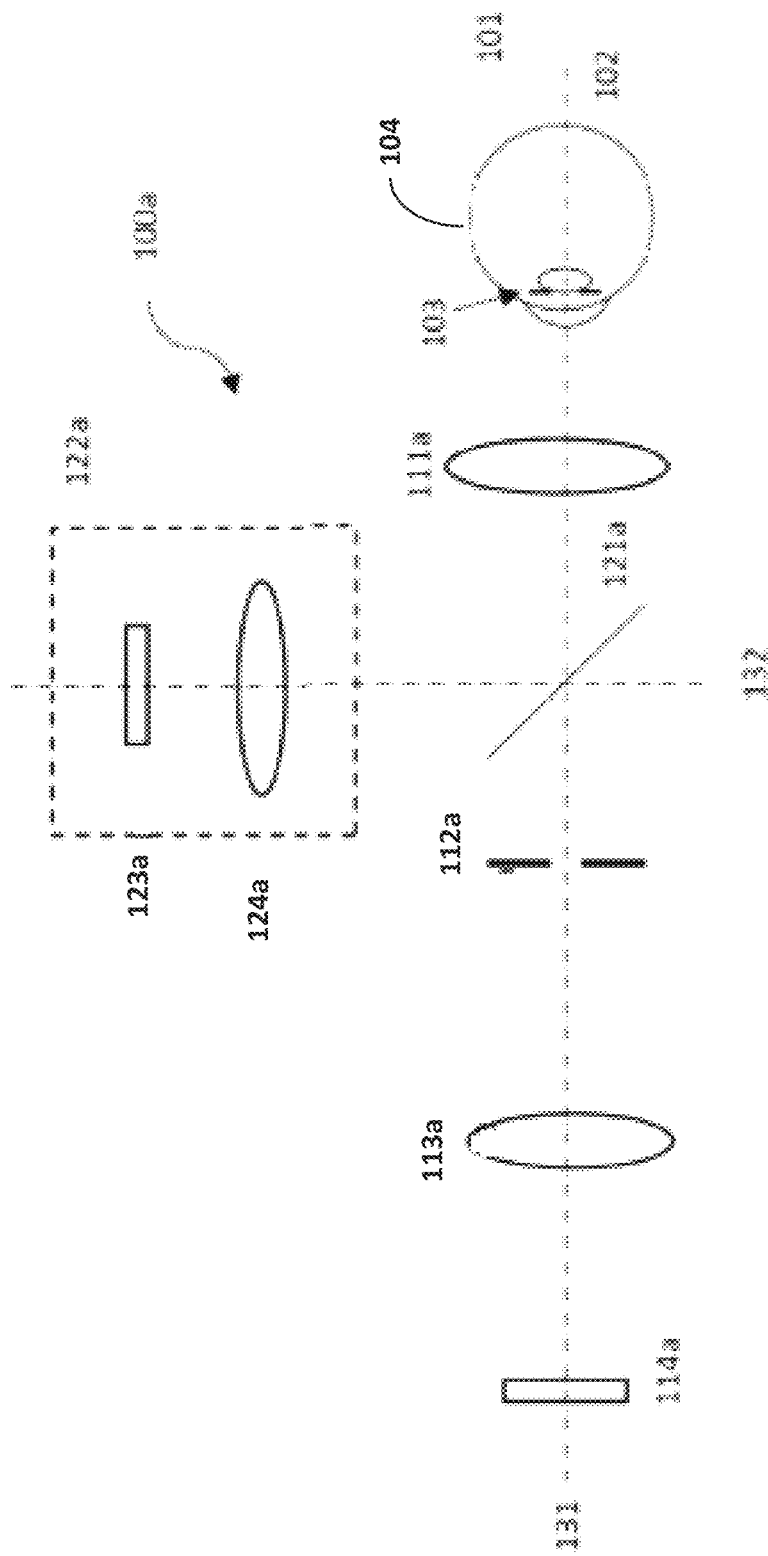
FIGS. 1A and 1B are diagrammatic side views illustrating example embodiments of optical configurations of systems of retinal 3D imaging.

The following disclosure describes various embodiments of the present invention and method of use in at least one of its preferred, best mode embodiments, which is further defined in detail in the following description. Those having ordinary skill in the art may be able to make alterations and modifications to what is described herein without departing from its spirit and scope. While this invention is susceptible to different embodiments in different forms, there is illustrated in the drawings and will herein be described in detail a preferred embodiment of the invention with the understanding that the present disclosure is to be considered as an exemplification of the principles of the invention and is not intended to limit the broad aspect of the invention to the embodiment illustrated. All features, elements, components, functions, and steps described with respect to any embodiment provided herein are intended to be freely combinable and substitutable with those from any other embodiment unless otherwise stated. Therefore, it should be understood that what is illustrated is set forth only for the purposes of example and should not be taken as a limitation on the scope of the present invention.

In the following description and in the figures, like elements are identified with like reference numerals. The use of "e.g.," "etc.," and "or" indicates non-exclusive alternatives without limitation, unless otherwise noted. The use of "including" or "includes" means "including, but not limited to," or "includes, but not limited to," unless otherwise noted.

As used herein and in the appended claims, the singular forms "a," "an," and "the" include plural referents unless the context clearly dictates otherwise.

In general, terms such as "coupled to," and "configured for coupling to," and "secure to," and "configured for securing to" and "in communication with" (for example, a first component is "coupled to" or "is configured for coupling to" or is "configured for securing to" or is "in communication with" a second component) are used herein to indicate a structural, functional, mechanical, electrical, signal, optical, magnetic, electromagnetic, ionic or fluidic relationship between two or more components or elements. As such, the fact that one component is said to be in communication with a second component is not intended to exclude the possibility that additional components may be present between, and/or operatively associated or engaged with, the first and second components.

Systems for 2D retinal imaging are described in the application PCT/US2019/063230 (incorporated here by reference) and some modifications made to integrate a system for 2D retinal imaging with a system for 3D retinal imaging are described in examples disclosed in this application.

Example Embodiments of Optical Configurations for Systems of Retinal 3D Imaging.

Figure 1B:
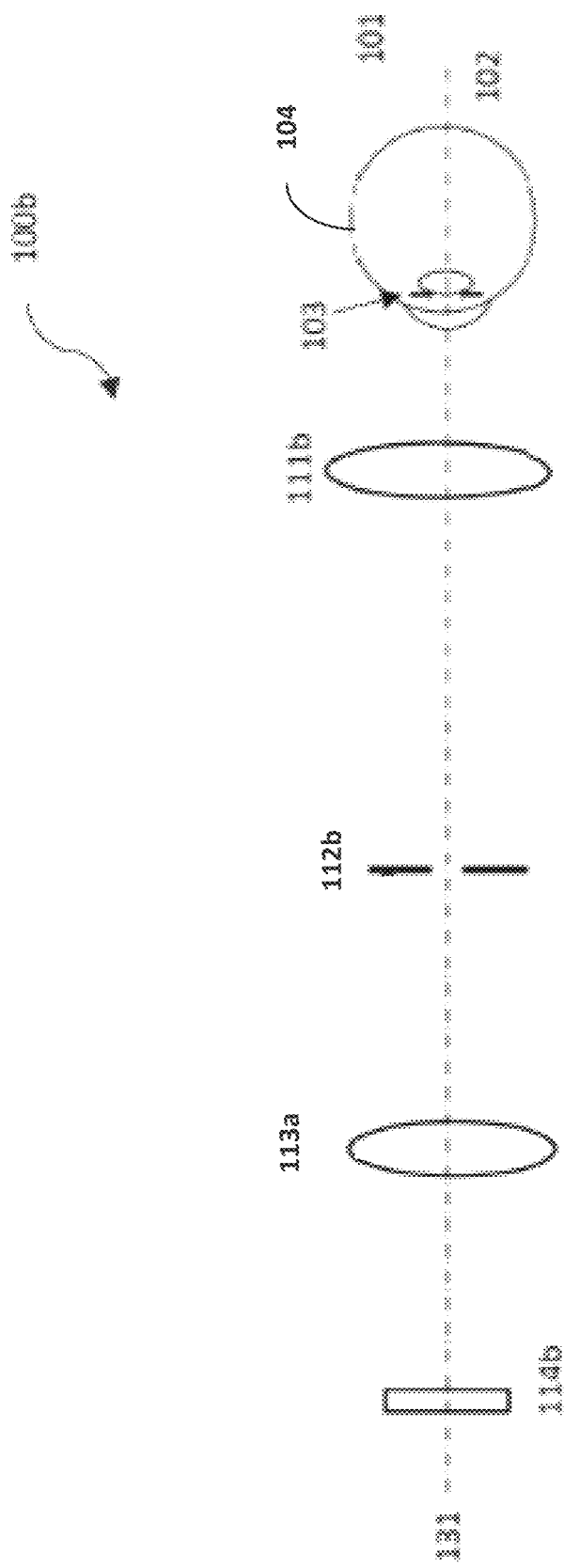

Example embodiments of optical configurations that may be used for systems of retinal 3D imaging will be described. FIGS. 1A and 1B are diagrammatic side views of various example embodiments of optical configurations for systems of retinal 3D imaging.

FIG. 1A is a diagrammatic side view illustrating an embodiment of an optical configuration of a system of retinal 3D imaging 100a. According to some embodiments, a system of retinal 3D imaging may be configured to perform 3D imaging of a retina 102 of an eye 101 providing the topographical information of the retina. According to some embodiments, the system of retinal 3D imaging may perform not only retinal 3D imaging but also 2D retinal imaging. In some embodiments, an optical axis 131 of the system of retinal 3D imaging 100a may be configured in a coaxial relationship with the optical system of an eye and an optical axis 132 of the system of retinal 3D imaging and an axis of the optical system of an eye may be configured to meet at a right angle (90°) to acquire high quality retinal images using the embodiments of optical design pupil layouts 103a to 103d which will be described later (FIGS. 2A to 2D). In some embodiments, an optical axis 131 of the system of retinal 3D imaging may be offset by a predetermined distance from the optical system of an eye to acquire high quality retinal images using other embodiments of optical design pupil layouts.

According to some embodiments, the optical configuration of a system of retinal 3D imaging 100a may include certain optical elements, including a 3D structured light illumination module 122a, an optical component 121a, an objective lens 111a, a baffle-and-illumination module 112a, a reimaging corrective optics module 113a, and an image sensor 114a.

The 3D structured light illumination module 122a may include one or more 3D structured light sources 123a and a collimation optical sub-system 124a. The collimation optical sub-system 124a may include one or more optical elements, such as one or more lenses. The collimation optical sub-system 124a may be used to collimate a beam from the one or more 3D structured light sources 123a. Collimation is the process of making light rays parallel, the adjustment or alignment of optical axes.

The optical component 121a may be a beam splitter or dichroic mirror. A beam splitter may be any device for dividing a beam of light or other electromagnetic radiation into two or more separate beams. In its most common form, a cube, a beam splitter may be made from two triangular glass prisms which may be glued together at their base using polyester, epoxy, or urethane-based adhesives. Another design may use of a half-silvered mirror. The half-silvered mirror may include an optical substrate, which may be a sheet of glass or plastic, with a partially transparent thin coating of metal. The thin coating may be aluminum deposited from aluminum vapor using a physical vapor deposition method. The thickness of the deposit may be controlled so that part (e.g., half) of the light, which is incident at a 45-degree angle and not absorbed by the coating or substrate material, is transmitted and the remainder is reflected. A dichroic mirror (or dual-band mirror, dual-wavelength mirror, dichroic reflector) is a mirror with significantly different reflection or transmission properties at two different wavelengths. The two wavelength regions of some may often not have a large width.

The objective lens 111a may include a lens or system of lenses that form an image of an object. The objective lens 111a may be an optical element that gathers light from the object being observed, e.g., the eye, and focuses the light rays to produce a real image. Objective lens 111a may be a single lens or a combination of several optical elements.

The baffle-and-illumination module 112a may include any device used to prevent the spreading of sound or light in a particular direction. For example, a device such as a plate or screen, used to deflect, check, or regulate flow or passage of light.

The reimaging corrective optics module 113a may be a series of one or more optical elements configured to correct aberrations of a retinal image before the retinal image reaches an image sensor 114a, which may improve the image resolution, adjust diopter, adjust astigmatism, adjust focus, change an image magnification for retinal 3D imaging, or some combination of improve the image resolution, adjust diopter, adjust astigmatism, and adjust focus, change an image magnification for retinal 3D imaging. In an example embodiment, the reimaging corrective optics module 113a may be multiple optical components such as a series of lenses.

The image sensor 114a may include any imaging sensor capable of collecting image data on, e.g., an image of an eye or a portion of an eye. For example, in one embodiment, the image sensor 114a may include any imaging sensor capable of collecting image data on a human eye. Other examples may be used for imaging animals or other creature's eyes.

According to another aspect of the embodiments, a 3D structured light illumination module 122a may include one or more 3D structured light sources 123a and a collimation optical sub-system 124a. The 3D structured light source 123a may be configured to operate in a multitude of spectrum ranges (e.g., white light, red light, green light, blue light, near infrared (IR) light) which may include one or more components of, for example, digital light processing projectors, digital video projectors, liquid-crystal-on-silicon chips, and vertical-cavity surface-emitting lasers (VCSELs).

According to some embodiments, a collimation optical sub-system 124a may be configured to include one or more optical components, for example, lenses, optical fibers, and waveguides. The collimation optical sub-system 124a may use the one or more optical components to generate a certain shape and size of an area of structured light illumination. The certain shape and size of an area of structured light illumination may be selected depending on the optical design pupil layout chosen (e.g., at or near the pupil plane of an eye) for the system of retinal 3D imaging. The optical design pupil layout 103a to 103d may include one of embodiments. According to other embodiments, the collimation optical sub-system 124a may be configured to use one or more electroactive lenses or electronically focus-tunable lenses to acquire focused images at various depths of a retina.

According to some embodiments, an objective lens 111a may be configured to focus a pattern of illumination 3D structured light onto or near an eye pupil plane and illuminate a retina. In some embodiments, a system of retinal 3D imaging may perform not only retinal 3D imaging but also 2D retinal imaging. Additionally, the objective lens 111a may be configured to be able to focus a pattern of 3D structured light illumination from the 3D structured light illumination module 122a onto or near an eye pupil plane and a pattern of illumination from the baffle-and-illumination module 112a to illuminate a retina.

According to some embodiments, the pattern of illumination for retinal 3D imaging and the pattern of illumination for retinal 2D imaging may include one or more separate arc-shapes, one or more separate race-track shapes, one or more separate rectangles, one or more parts of circles, one or more circular shapes or a combination of rectangles, rectangular shapes, parts of circles, or circular shapes. The patterns of illumination of 2D retinal imaging and retinal 3D imaging may be the same or may be different.

In some embodiments, the objective lens 111a may also be configured to relay, image, or relay and image the pupil of an eye onto an aperture of a baffle-and-illumination module 112a for retinal 3D imaging. The objective lens 111a may also be configured to image a plurality of imaging rays travelling from the retina through the pupil of an eye. The imaging rays travelling from the retina through the pupil of an eye may be in an advantageous position. The position may allow corrective optics module 113a to image the retina onto an image sensor 114a (e.g., for a relaxed eye) for retinal 3D imaging.

In some embodiments, the system of retinal 3D imaging may perform not only retinal 3D imaging but also 2D retinal imaging and the objective lens 111a may also be configured to relay, image, or relay and image the pupil of an eye onto an aperture of a baffle-and-illumination module and image a plurality of imaging rays travelling from the retina through the pupil of an eye, which may allow a reimaging corrective optics module 113a to image the retina onto an image sensor 114a (e.g., for a relaxed eye) for both retinal 3D imaging and retinal 2D imaging. The optical elements comprising an objective lens 111a may be located between a pupil plane 103 of an eye and an optical component 121a.

In some embodiments, for example, the objective lens 111a may be configured to capture the plurality of imaging rays from the retina of an eye with a field of view of about 10°×10° to about 20°×20° for retinal 3D imaging. In some embodiments, the system of retinal 3D imaging may perform not only retinal 3D imaging but also 2D retinal imaging for example, objective lens 111a may be configured to capture the plurality of imaging rays from the retina of an eye with a field of view of about 10°×10° to about 20°×20° for retinal 3D imaging and 60°×60° for 2D retinal imaging. According to another aspect of the embodiments, the optical component 121a may be a beam splitter or dichroic mirror.

According to some embodiments, a baffle-and-illumination module 112a may include one or more baffles. The baffle(s) may be an opaque structure with a hole aperture located therein and the baffle(s) may be configured to block partial reflections of undesired reflected light from the cornea of an eye, stray light other than the reflected light from the retina being imaged in 3D retinal images, or both block partial reflections of undesired reflected light from the cornea of an eye and stray light other than the reflected light from the retina being imaged in 3D retinal images, e.g., in both 3D retinal images and 2D retinal images. The baffle-and-illumination module 112a may be located between an optical component 121a and a reimaging corrective optics module 113a, as illustrated in FIG. 1A.

In some embodiments, the baffle-and-illumination module 112a may include one or more illumination sub-systems, wherein the illumination sub-systems may be configured to include a 3D structured light illumination module for retinal 3D imaging. In other embodiments, the illumination sub-systems may be configured to provide illumination for 2D retinal imaging. In some embodiments, the illumination sub-systems may be configured to provide illumination for both 3D retinal imaging and 2D retinal imaging. According to some embodiments, the illumination sub-systems may be configured to illuminate a retina of an eye through areas allocated for illumination on or near the eye pupil plane. Imaging rays reflected from the retina may pass through the aperture of baffle-and-illumination module 112a and a reimaging corrective optics module 113a to be imaged onto an image sensor 114a after being collected by objective lens 111a.

In some embodiments, the illumination sub-system(s) may include one or more light emitting diodes ("LEDs"). In some embodiments, the illumination sub-system(s) may include one or more VCSELs. In some embodiments, the illumination sub-system(s) may include a combination of one or more LEDs and one or more VCSELs. According to some embodiments, the illumination sub-system(s) may be configured to operate in a multitude of spectrum ranges (e.g., white, red, green, blue, near IR), and one or more waveguides configured to generate an emission shape and size depending on the optical design pupil layout chosen (e.g., at or near the pupil plane of an eye) for each illumination sub-system. The optical design pupil layout 103a to 103d may include one of embodiments.

According to some embodiments, as discussed above, a reimaging corrective optics module 113a may be configured to correct aberrations of a retinal image before the retinal image reaches an image sensor 114a, which may improve the image resolution, adjust diopter, adjust astigmatism, adjust focus, change an image magnification for retinal 3D imaging, or some combination of improve the image resolution, adjust diopter, adjust astigmatism, and adjust focus, change an image magnification for retinal 3D imaging. According to some embodiments, a system of retinal 3D imaging may perform not only retinal 3D imaging but also 2D retinal imaging and a reimaging corrective optics module 113a may be configured to correct aberrations of a retinal image before the retinal image reaches an image sensor 114a, which may improve the image resolution, adjust diopter, adjust astigmatism, adjust focus, change an image magnification for both retinal 3D imaging and 2D retinal imaging, or some combination of improve the image resolution, adjust diopter, adjust astigmatism, adjust focus, and change an image magnification for both retinal 3D imaging and 2D retinal imaging.

According to some embodiments, the reimaging corrective optics module 113a may include multiple optical components such as a series of lenses. The reimaging corrective optics module 113a may be located between the baffle-and-illumination module 112a and an image sensor 114a. In some embodiments, image sensor 114a may be located at a final image plane for retinal 3D imaging. In other embodiments, a system of retinal 3D imaging may perform not only retinal 3D imaging but also 2D retinal imaging and image sensor 114a may be located at a final image plane for both retinal 3D imaging and 2D retinal imaging.

Referring to FIG. 1B, in some embodiments, an optical configuration for retinal 3D imaging 100b may perform retinal 3D imaging and may not use the 3D structured light illumination module 122*a* and optical component 121*a* (as illustrated in FIG. 1B). The optical configuration for retinal 3D imaging 100*b* may include one or more 3D structured light illumination source(s) and a collimation optical sub-system in a baffle-and-illumination module 112*b*. Some embodiments may use smaller optical components, for example of strip pattern VCSELs. In other embodiments, optical configuration for retinal 3D imaging 100*b* may perform not only retinal 3D imaging but also retinal 2D imaging and the baffle-and-illumination module 112*b* includes one or more 3D structured light illumination source(s), a collimation optical sub-system for retinal 3D imaging and one or more illumination sub-systems for retinal 2D imaging.

An aspect may include an optical component between the objective lens and the baffle-and-illumination module, and a 3D structured light illumination module optically coupled to the optical component. Optically coupled may include being coupled together by light or other waves of the electromagnetic spectrum.

In an aspect, the collimation optical sub-system generates an area of structured light illumination. Structured light or structured illumination may refer to a projection of light with a known shading pattern. The result may be the projection of a known light pattern on the captured scene. Accordingly, the collimation optical sub-system may generate a projection of light with a known shading pattern.

In an aspect, the reimaging corrective optics module corrects aberrations of a retinal image before the retinal image reaches the image sensor. In other words, the reimaging corrective optics module may remove or lessen aberrations of a retinal image before the retinal image reaches the image sensor.

Example Embodiments of Optical Design Pupil Layout for Systems of Retinal 3D Imaging Example embodiments of optical design pupil layouts that may be used for systems of retinal 3D imaging will be described. FIGS. 2A to 2D are diagrams of various example embodiments of optical design pupil layouts of systems of retinal 3D imaging of the present disclosure.

Figure 2A:
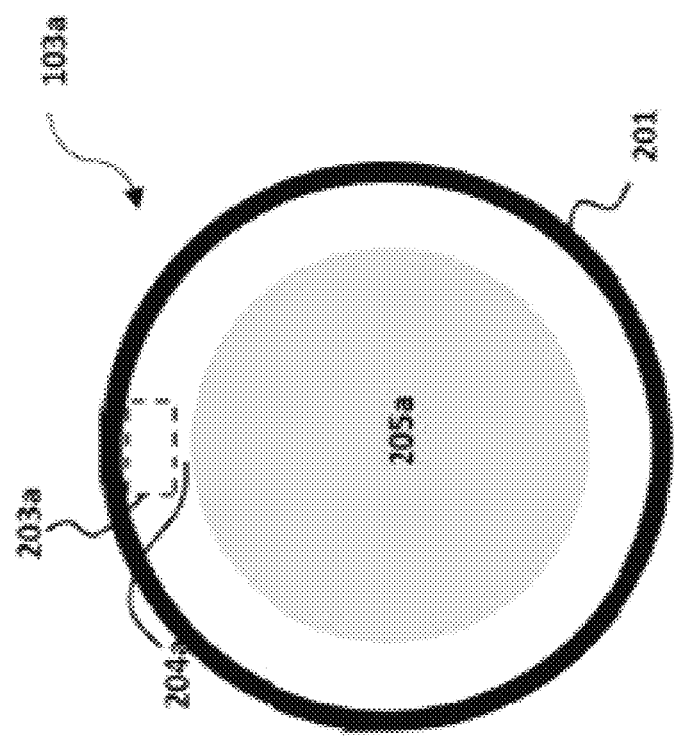
FIGS. 2A to 2D are diagrams of example embodiments of optical design pupil layouts for systems of retinal 3D imaging.

FIG. 2A is a diagram illustrating an example embodiment of an optical design pupil layout 103*a* on or near pupil 104 of an eye that may be used for a plurality of optical configurations of systems of retinal 3D imaging (e.g., the system of retinal 3D imaging 100*a*, 100*b* of FIGS. 1A and 1B). According to some embodiments, a system of retinal 3D imaging may be configured to image 3D structured light illumination on or near a pupil plane 103 of an eye. The pupil boundary 201 of an eye may be the conjugate to the aperture stop of the system of retinal 3D imaging. According to other aspects of optical design pupil layout 103*a*, an area 203*a* at or near the pupil plane 103 of an eye may be allocated for an illumination patch from a 3D structured light illumination module to illuminate a retina, and an area in a middle portion 205*a* (e.g., at or near the pupil 104 of an eye) may be configured for imaging rays to pass through toward a baffle-and-illumination module from the retina of an eye with a distance of buffer area 204*a* between the area 203*a* and the middle portion 205*a*.

Figure 2B:
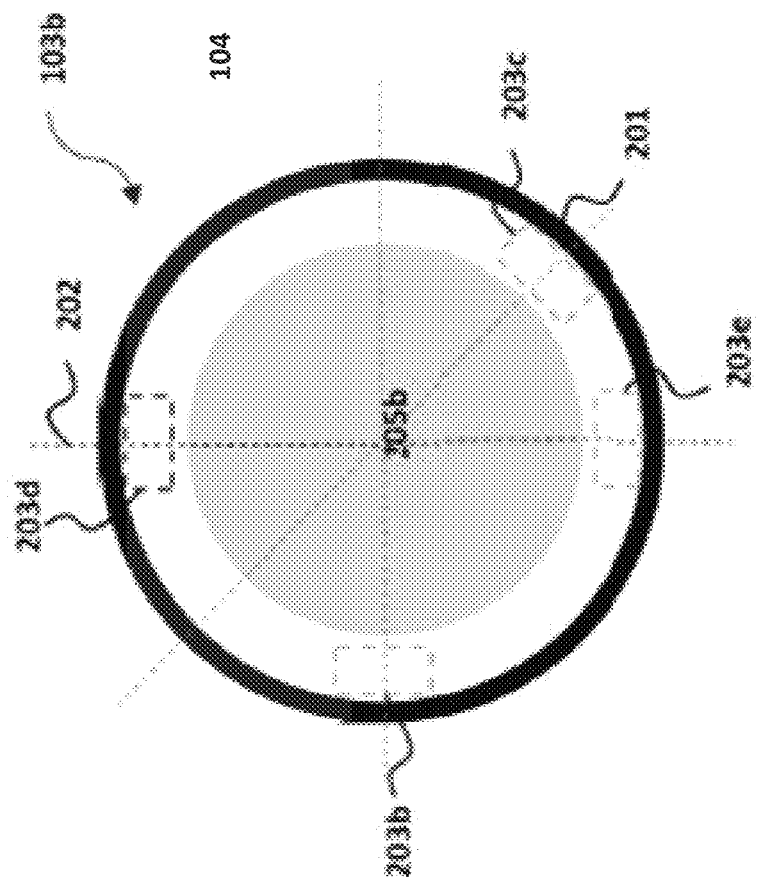

FIG. 2B is a diagram illustrating an example embodiment of an optical design pupil layout 103*b* on or near pupil 104 of an eye that may be used for a plurality of optical configurations of systems of retinal 3D imaging (e.g., the system of retinal 3D imaging 100*a*, 100*b* of FIGS. 1A and 1B). According to some aspects of optical design pupil layout 103*b*, a vertical reference line 202 is provided to illustrate the angle and direction of the example embodiments of an optical design pupil layout. Those of skill in the art will recognize that the illumination from the 3D structured light illumination module may be positioned at different angles with respect to the vertical reference line 202, other than 0°. For example, the illumination patch, e.g., in area 203*d* may be replaced by the area 203*b* or area 203*c*. The shape of the area for illumination patch may be a different shape than a rectangle such as a shape comprising one or more separate arc-shapes, one or more separate race-track shapes, one or more separate rectangles, or a combination of rectangles, rectangular shapes, parts of circles, or circular shapes.

According to certain embodiments of optical design pupil layout 103*b*, area 203*d* and area 203*e* or more areas, for example, area 203*b* to area 203*e* illustrated in FIG. 2B (e.g., at or near the pupil plane 103 of an eye) may be allocated for the areas for illumination patches from 3D structured light illumination module to illuminate a retina. When multiple illumination sub-systems are being used, as may be seen in FIG. 2B, according to some embodiments, only the upper illumination sub-system, e.g., in area 203*d* (see FIG. 2B) may be active and other illumination sub-systems, for example, illumination sub-systems, e.g., in area 203*b*, area 203*c*, area 203*e*, or some combination of area 203*b*, area 203*c*, or area 203*e* (see FIG. 2B) may be inactive for retinal 3D imaging. According to another aspect of the embodiments, multiple images from different parts of a retina may be acquired by using each of multiple 3D structured light illumination modules for retinal 3D imaging. Multiple images may be captured subsequently.

Figure 2C:
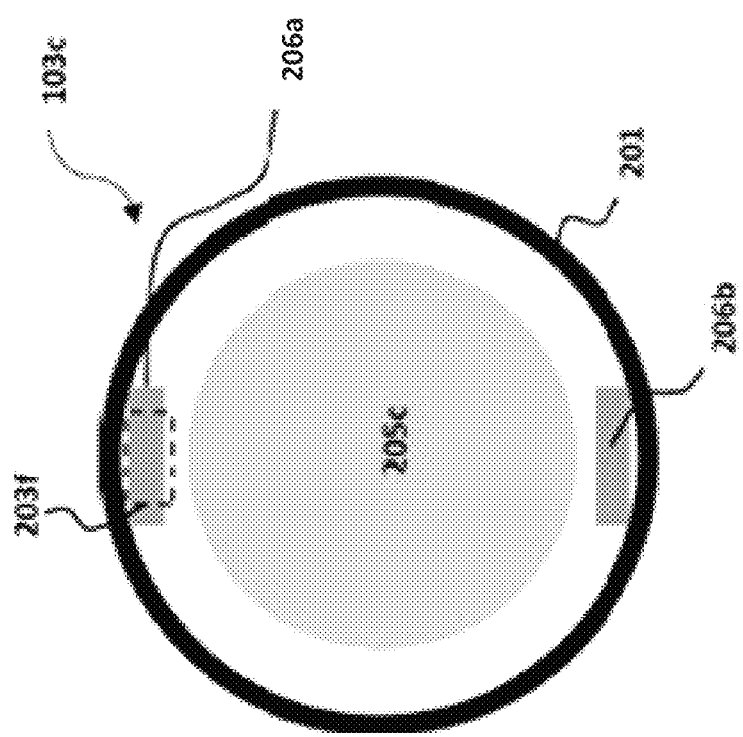

FIG. 2C is a diagram illustrating an example embodiment of an optical design pupil layout 103*c* on or near pupil 104 of an eye that may be used for a plurality of optical configurations of systems of retinal 3D imaging (e.g., the system of retinal 3D imaging 100*a*, 100*b* of FIGS. 1A and 1B). According to some aspects of optical design pupil layout 103*c*, an areas 203*f* at or near the pupil plane 103 of an eye (as illustrated in FIG. 2C) may be allocated for an illumination patch from 3D structured light illumination module to illuminate a retina for retinal 3D imaging, and an area 206*a* or multiple areas, for example, two areas, area 206*a* and area 206*b* may be allocated for the illumination patch(es) from an illumination sub-system to illuminate a retina for 2D retinal imaging. An area in a middle portion 205*c* (e.g., at or near the pupil 104 of eye) may be configured for imaging rays to pass through toward a baffle-and-illumination module from the retina of an eye.

Figure 2D:
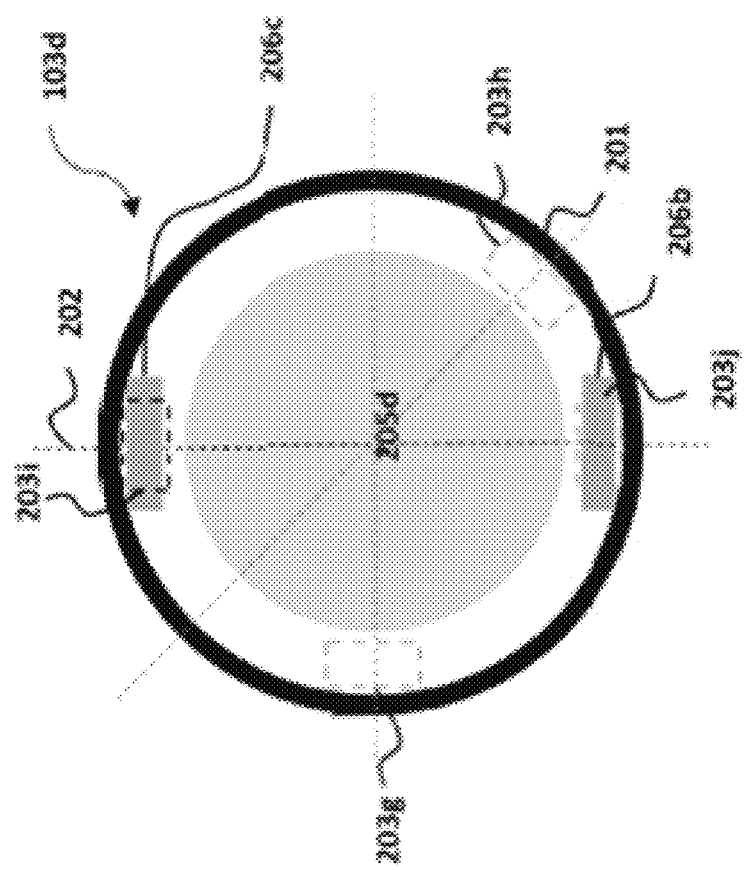

FIG. 2D is a diagram illustrating an example embodiment of an optical design pupil layout 103*d* on or near pupil 104 of an eye that may be used for a plurality of optical configurations of systems of retinal 3D imaging (e.g., the system of retinal 3D imaging 100*a*, 100*b* of FIGS. 1A and 1B). According to some aspects of optical design pupil layout 103*d*, a vertical reference line 202 is provided to illustrate the angle and direction of the example embodiments of an optical design pupil layout. Those of skill in the art will recognize that the illumination from the 3D structured light illumination module may be positioned at different angles with respect to the vertical reference line 202, other than 0°. For example, the illumination patch, e.g., in area 203*i* may be replaced by the area 203*g* or area 203*h*. The shape of illumination patch may be a different shape than a rectangle such as a shape comprising one or more separate arc-shapes, one or more separate race-track shapes, one or more separate rectangles, or a combination of rectangles, rectangular shapes, parts of circles, or circular shapes.

According to certain embodiments of optical design pupil layout 103d, two areas, area 203i and area 203d or more areas, for example, area 203g to area 203j illustrated in FIG. 2B (at or near the pupil plane 103 of an eye) may be allocated for the areas for illumination patches from 3D structured light illumination module to illuminate a retina for retinal 3D imaging. According to some aspects of optical design pupil layout 103d, an area 206c or multiple areas, for example, two areas 206c and 206d may be allocated for an illumination patch from illumination sub-system to illuminate a retina for 2D retinal imaging. When multiple illumination sub-systems are being used, as may be seen in FIG. 2D, in other embodiments, only the upper illumination sub-system, e.g., in area 203i (see FIG. 2D) may be active and other illumination sub-systems, e.g., in area 203g, area 203j, and area 203h (see FIG. 2D) may be inactive for retinal 3D imaging. According to another aspect of the embodiments, multiple images from different parts of a retina may be acquired by using each of multiple illumination sub-systems for retinal 3D imaging. According to another aspect of the embodiments, a system of retinal 3D imaging may perform not only retinal 3D imaging but also 2D retinal imaging and multiple images from different parts of a retina may be acquired by using each of multiple illumination sub-systems for 2D retinal imaging. Multiple images may be captured subsequently.

It should also be noted that all features, elements, components, functions, and steps described with respect to any embodiment provided herein are intended to be freely combinable and substitutable with those from any other embodiment. If a certain feature, element, component, function, or step is described with respect to only one embodiment, then it should be understood that that feature, element, component, function, or step may be used with every other embodiment described herein unless explicitly stated otherwise. This paragraph therefore serves as antecedent basis and written support for the introduction of claims, at any time, that combine features, elements, components, functions, and steps from different embodiments, or that substitute features, elements, components, functions, and steps from one embodiment with those of another, even if the following description does not explicitly state, in a particular instance, that such combinations or substitutions are possible. It is explicitly acknowledged that express recitation of every possible combination and substitution is overly burdensome, especially given that the permissibility of each and every such combination and substitution will be readily recognized by those of ordinary skill in the art.

To the extent the embodiments disclosed herein include or operate in association with memory, storage, and/or computer-readable media, then that memory, storage, and/or computer-readable media are non-transitory. Accordingly, to the extent that memory, storage, and/or computer-readable media are covered by one or more claims, then that memory, storage, and/or computer-readable media is only non-transitory.

While the embodiments are susceptible to various modifications and alternative forms, specific examples thereof have been illustrated in the drawings and are herein described in detail. It should be understood, however, that these embodiments are not to be limited to the particular form disclosed, but to the contrary, these embodiments are to cover all modifications, equivalents, and alternatives falling within the spirit of the disclosure. Furthermore, any features, functions, steps, or elements of the embodiments may be recited in or added to the claims, as well as negative limitations that define the inventive scope of the claims by features, functions, steps, or elements that are not within that scope.

It is to be understood that this disclosure is not limited to the particular embodiments described herein, as such may, of course, vary. It is also to be understood that the terminology used herein is for the purpose of describing particular embodiments only and is not intended to be limiting.

Various aspects have been presented in terms of systems that may include several components, modules, and the like. It is to be understood and appreciated that the various systems may include additional components, modules, etc. and/or may not include all the components, modules, etc. discussed in connection with the figures. A combination of these approaches may also be used. The various aspects disclosed herein may be performed on electrical devices including devices that utilize touch screen display technologies and/or mouse-and-keyboard type interfaces. Examples of such devices include computers (desktop and mobile), smart phones, personal digital assistants (PDAs), and other electronic devices both wired and wireless.

In addition, the various illustrative logical blocks, modules, and circuits described in connection with the aspects disclosed herein may be implemented or performed with a general purpose processor, a digital signal processor (DSP), an application specific integrated circuit (ASIC), a field programmable gate array (FPGA) or other programmable logic device, discrete gate or transistor logic, discrete hardware components, or any combination thereof designed to perform the functions described herein. A general-purpose processor may be a microprocessor, but in the alternative, the processor may be any conventional processor, controller, microcontroller, or state machine. A processor may also be implemented as a combination of computing devices, e.g., a combination of a DSP and a microprocessor, a plurality of microprocessors, one or more microprocessors in conjunction with a DSP core, or any other such configuration.

Operational aspects disclosed herein may be embodied directly in hardware, in a software module executed by a processor, or in a combination of the two. A software module may reside in random access memory (RAM) memory, flash memory, read only memory (ROM) memory, erasable programmable read only memory (EPROM) memory, electrically erasable programmable read only memory (EEPROM) memory, registers, hard disk, a removable disk, a Compact Disk Read Only Memory (CD-ROM), or any other form of storage medium known in the art. An exemplary storage medium is coupled to the processor such the processor may read information from, and write information to, the storage medium. In the alternative, the storage medium may be integral to the processor. The processor and the storage medium may reside in an ASIC. The ASIC may reside in a user terminal. In the alternative, the processor and the storage medium may reside as discrete components in a user terminal.

Furthermore, the one or more versions may be implemented as a method, apparatus, or article of manufacture using standard programming and/or engineering techniques to produce software, firmware, hardware, or any combination thereof to control a computer to implement the disclosed aspects. A non-transitory computer-readable medium may include any non-transitory computer-readable media, such as, but are not limited to magnetic storage devices (e.g., hard disk, floppy disk, magnetic strips . . . ), optical disks (e.g., compact disk (CD), digital versatile disk (DVD), BluRay™ . . . ), smart cards, solid-state devices (SSDs), and flash memory devices (e.g., card, stick). Of course, those skilled in the art will recognize many modifications may be made to this configuration without departing from the scope of the disclosed aspects.

One or more of the components, steps, features, and/or functions illustrated in the figures may be rearranged and/or combined into a single component, block, feature, or function or embodied in several components, steps, or functions. Additional elements, components, steps, and/or functions may also be added without departing from the disclosure. The apparatus, devices, and/or components illustrated in the figures may be configured to perform one or more of the methods, features, or steps described in the figures. The algorithms described herein may also be efficiently implemented in software and/or embedded in hardware.

Reference in the specification to "one embodiment" or "an embodiment" means that a particular feature, structure, or characteristic described in connection with the embodiment is included in at least one embodiment of the invention. The appearances of the phrase "in one embodiment" in various places in the specification are not necessarily all referring to the same embodiment.

Some portions of the detailed description are presented in terms of algorithms and symbolic representations of operations on data bits within a computer memory. These algorithmic descriptions and representations are the methods used by those skilled in the data processing arts to most effectively convey the substance of their work to others skilled in the art. An algorithm is here, and generally, conceived to be a self-consistent sequence of steps leading to a desired result. The steps are those requiring physical manipulations of physical quantities. Usually, though not necessarily, these quantities take the form of electrical or magnetic signals capable of being stored, transferred, combined, compared or otherwise manipulated. It has proven convenient at times, principally for reasons of common usage, to refer to these signals as bits, values, elements, symbols, characters, terms, numbers or the like.

It should be borne in mind, however, that all of these and similar terms are to be associated with the appropriate physical quantities and are merely convenient labels applied to these quantities. Unless specifically stated otherwise as apparent from the following disclosure, it is appreciated that throughout the disclosure terms such as "processing," "computing," "calculating," "determining," "displaying" or the like, refer to the action and processes of a computer system, or similar electronic computing device, that manipulates and transforms data represented as physical (electronic) quantities within the computer system's registers and memories into other data similarly represented as physical quantities within the computer system's memories or registers or other such information storage, transmission or display.

Finally, the algorithms and displays presented herein are not inherently related to any particular computer or other apparatus. Various general-purpose systems may be used with programs in accordance with the teachings herein, or it may prove convenient to construct more specialized apparatus to perform the method steps. The structure for a variety of these systems will appear from the description below. It will be appreciated that a variety of programming languages may be used to implement the teachings of the invention as described herein.

The figures and the following description describe certain embodiments by way of illustration only. One skilled in the art will readily recognize from the following description that alternative embodiments of the structures and methods illustrated herein may be employed without departing from the principles described herein. Reference will now be made in detail to several embodiments, examples of which are illustrated in the accompanying figures. It is noted that wherever practicable similar or like reference numbers may be used in the figures to indicate similar or like functionality.

The foregoing description of the embodiments of the present invention has been presented for the purposes of illustration and description. It is not intended to be exhaustive or to limit the present invention to the precise form disclosed. Many modifications and variations are possible in light of the above teaching. It is intended that the scope of the present invention be limited not by this detailed description, but rather by the claims of this application. As will be understood by those familiar with the art, the present invention may be embodied in other specific forms without departing from the spirit or essential characteristics thereof. Likewise, the particular naming and division of the modules, routines, features, attributes, methodologies and other aspects are not mandatory or significant, and the mechanisms that implement the present invention or its features may have different names, divisions and/or formats.

Furthermore, as will be apparent to one of ordinary skill in the relevant art, the modules, routines, features, attributes, methodologies and other aspects of the present invention may be implemented as software, hardware, firmware or any combination of the three. Also, wherever a component, an example of which is a module, of the present invention is implemented as software, the component may be implemented as a standalone program, as part of a larger program, as a plurality of separate programs, as a statically or dynamically linked library, as a kernel loadable module, as a device driver, and/or in every and any other way known now or in the future to those of ordinary skill in the art of computer programming.

Additionally, the present invention is in no way limited to implementation in any specific programming language, or for any specific operating system or environment. Accordingly, the disclosure of the present invention is intended to be illustrative, but not limiting, of the scope of the present invention, which is set forth in the following claims.

It is understood that the specific order or hierarchy of blocks in the processes/flowcharts disclosed is an illustration of example approaches. Based upon design preferences, it is understood that the specific order or hierarchy of blocks in the processes/flowcharts may be rearranged. Further, some blocks may be combined or omitted. The accompanying method claims present elements of the various blocks in a sample order and are not meant to be limited to the specific order or hierarchy presented.

The previous description is provided to enable any person skilled in the art to practice the various aspects described herein. Various modifications to these aspects will be readily apparent to those skilled in the art, and the generic principles defined herein may be applied to other aspects. Thus, the claims are not intended to be limited to the aspects illustrated herein but is to be accorded the full scope consistent with the language claims, wherein reference to an element in the singular is not intended to mean "one and only one" unless specifically so stated, but rather "one or more." The word "exemplary" is used herein to mean "serving as an example, instance, or illustration." Any aspect described herein as "exemplary" is not necessarily to be construed as preferred or advantageous over other aspects. Unless specifically stated otherwise, the term "some" refers to one or more. Combinations such as "at least one of A, B, or C," "one or more of A, B, or C," "at least one of A, B, and C," "one or more of A, B, and C," and "A, B, C, or any combination thereof" include any combination of A, B, and/or C, and may include multiples of A, multiples of B, or multiples of C. Specifically, combinations such as "at least one of A, B, or C," "one or more of A, B, or C," "at least one of A, B, and C," "one or more of A, B, and C," and "A, B, C, or any combination thereof" may be A only, B only, C only, A and B, A and C, B and C, or A and B and C, where any such combinations may contain one or more member or members of A, B, or C. All structural and functional equivalents to the elements of the various aspects described throughout this disclosure that are known or later come to be known to those of ordinary skill in the art are expressly incorporated herein by reference and are intended to be encompassed by the claims. Moreover, nothing disclosed herein is intended to be dedicated to the public regardless of whether such disclosure is explicitly recited in the claims. The words "module," "mechanism," "element," "device," and the like may not be a substitute for the word "means." As such, no claim element is to be construed as a means plus function unless the element is expressly recited using the phrase "means for."

The invention claimed is:

1. A system of retinal three-dimensional (3D) imaging, comprising:
   an image sensor within a light path;
   a reimaging corrective optics module within the light path, comprising multiple optical elements configured to correct aberrations, adjust diopter, adjust astigmatism, and adjust focus of a retinal image before the retinal image reaches the image sensor;
   an objective lens in the light path, configured to:
     focus a pattern of 3D structured light illumination from a 3D structured light illumination module onto or near an eye pupil plane; and
     relay and image the pupil of an eye onto an aperture of a baffle-and-illumination module; and
   a baffle-and-illumination module in the light path, located between the objective lens and the reimaging corrective optics module, the baffle-and-illumination module comprising:
     one or more baffles comprising an opaque structure with a hole aperture to block partial reflections of undesired light from the cornea and stray light other than the reflected light from the retina; and
     one or more illumination sub-systems configured to operate in a spectrum range including at least one of white light, red light, green light, blue light, or near infrared light.

2. The system of retinal 3D imaging of claim 1, further comprising: an optical component between the objective lens and the baffle-and-illumination module; and the 3D structured light illumination module optically coupled to the optical component.

3. The system of retinal 3D imaging of claim 2, wherein the 3D structured light illumination module includes: a 3D structured light source; and a collimation optical sub-system in a light path between the 3D structured light sources and the optical component.

4. The system of retinal 3D imaging of claim 3, wherein the 3D structured light source is configured to operate in a spectrum range comprising at least one of white light, red light, green light, blue light, and near infrared (IR) light.

5. The system of retinal 3D imaging of claim 3, wherein the collimation optical sub-system includes one or more optical components.

6. The system of retinal 3D imaging of claim 5, wherein the one or more optical components comprises at least one of a lens, an optical fiber, and a waveguide.

7. The system of retinal 3D imaging of claim 6, wherein the collimation optical sub-system generates an area of structured light illumination.

8. The system of retinal 3D imaging of claim 7, wherein the area of structured light illumination is selected depending on an optical design pupil layout chosen.

9. The system of retinal 3D imaging of claim 3, wherein the collimation optical sub-system includes one or more electroactive lenses or one or more electronically focus-tunable lenses.

10. The system of retinal 3D imaging of claim 9, wherein the one or more electroactive lenses or the one or more electronically focus-tunable lenses are configured to acquire focused images at various depths of a retina.

11. The system of retinal 3D imaging of claim 1, wherein the objective lens is configured to illuminate a retina.

12. The system of retinal 3D imaging of claim 2, wherein the objective lens is further configured to focus a pattern of illumination from the baffle-and-illumination module to illuminate a retina.

13. The system of retinal 3D imaging of claim 1, wherein the objective lens is configured to image a plurality of imaging rays travelling from the retina through a pupil of an eye.

14. The system of retinal 3D imaging of claim 1, wherein, the one or more baffles configured to block partial reflections of undesired reflected light from a cornea of an eye and stray light other than the reflected light from the retina from being imaged in 3D retinal images.

15. The system of retinal 3D imaging of claim 1, wherein the reimaging corrective optics module corrects aberrations of a retinal image before the retinal image reaches the image sensor.

* * * * *